(12) United States Patent
Saito et al.

(10) Patent No.: US 7,846,745 B2
(45) Date of Patent: Dec. 7, 2010

(54) DEVICE FOR IMMUNOCHROMATOGRAPHY

(75) Inventors: Noriyuki Saito, Akashi (JP); Takahiro Taya, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 383 days.

(21) Appl. No.: 10/882,847

(22) Filed: Jun. 30, 2004

(65) Prior Publication Data

US 2004/0266024 A1  Dec. 30, 2004

(30) Foreign Application Priority Data

Jun. 30, 2003  (JP)  ............... 2003-188068
Jun. 30, 2003  (JP)  ............... 2003-188069

(51) Int. Cl.
*G01N 33/53* (2006.01)

(52) U.S. Cl. ............. 436/514; 436/518; 436/810; 435/287.1; 435/287.7; 435/287.8; 435/970; 422/56; 422/58; 422/59; 422/60

(58) Field of Classification Search .......... 436/518, 436/514, 65, 164, 169, 510, 524, 528, 805, 436/810; 435/7.1, 7.91, 287.1, 287.7, 287.8, 435/970; 422/56–60
See application file for complete search history.

(56) References Cited

U.S. PATENT DOCUMENTS

| 4,857,453 | A | * | 8/1989 | Ullman et al. ............. 435/7.92 |
| 4,861,711 | A |   | 8/1989 | Friesen et al. |
| 4,943,522 | A | * | 7/1990 | Eisinger et al. ............ 435/7.25 |
| 5,434,087 | A | * | 7/1995 | Beggs et al. ................ 436/505 |
| 5,602,040 | A |   | 2/1997 | May et al. |
| 5,622,871 | A |   | 4/1997 | May et al. |
| 5,656,503 | A |   | 8/1997 | May et al. |
| 5,821,073 | A | * | 10/1998 | Lee .......................... 435/7.92 |
| 6,187,598 | B1 |  | 2/2001 | May et al. |
| 6,228,660 | B1 |  | 5/2001 | May et al. |
| 2001/0008774 | A1 | | 7/2001 | May et al. |
| 2001/0041368 | A1 | | 11/2001 | May et al. |

FOREIGN PATENT DOCUMENTS

| JP | 2002-328129 | 11/2002 |
| JP | 2002-328130 | 11/2002 |

* cited by examiner

*Primary Examiner*—Bao-Thuy L Nguyen
(74) *Attorney, Agent, or Firm*—Brinks Hofer Gilson & Lione

(57) ABSTRACT

Device for immunochromatography comprise a test strip comprising a sample application member, a label holding member and a chromatography membrane, a first case member and a second case member. Detection kits and methods for testing an analyte substance are also described.

12 Claims, 4 Drawing Sheets

DEVICE FOR IMMUNOCHROMATOGRAPHY

This application claims priority under 35 U.S.C. §119 to Japanese Patent Application Nos. 2003-188068 and 2003-188069 both filed Jun. 30, 2003, the entire contents of which are hereby incorporated herein by reference.

BACKGROUND

1. Field of the Invention

The present invention relates to a device for immunochromatography. More particularly, the present invention relates to a device for immunochromatography having a case that houses a test strip for immunochromatography.

2. Discussion of the Related Art

Hitherto, numerous reports have been made on immunochromatography as a method for conducting tests easily by using antigen-antibody reaction (U.S. Pat. Nos. 4,861,711, 5,602,040). The testing methods disclosed in these patent documents can reveal the absence or presence and the amount of an antigen by simply letting a collected specimen penetrate into a testing device containing an antibody corresponding to the target analyte substance (for example, antigen). These methods make use of a porous membrane such as nitrocellulose that contains a ligand (for example, specific antibody) corresponding to the target analyte substance at one end of the porous membrane and similarly contains, in a band-like manner, a different specific antibody that binds to a specific antigen which is the analyte substance in the middle of the porous membrane. The specific antibody contained at the one end is colored in advance. When a sample liquid is let to penetrate onto the one end of the porous membrane, if any antigen that reacts with the specific antibody is present in the sample liquid, the antigen binds with the specific antibody and moves along the porous membrane by capillary phenomenon towards the other end opposite to the side where the sample liquid has been let to penetrate, accompanied by the colored particles. At the time of passing through the site of the different specific antibody fixed in a band-like manner to the porous membrane during the movement, the antigen is captured by the specific antibody on the porous membrane, whereby a band-like stain appears on the porous membrane. This reveals the presence and the amount of the target antigen in the sample.

Regarding the technique of immunochromatography, numerous studies have been made and reported so as to make a good and facilitated detection of an analyte substance (Japanese Laid-open Patent Publications 2002-328129 and 2002-328130). However, these reports are on a test strip for immunochromatography testing, and are not on a device for immunochromatography including a testing case that houses a test strip.

SUMMARY

An object of the present invention is to provide a device for immunochromatography, which can achieve a speedy and facilitated test.

Another object of the present invention is to provide a device for immunochromatography, which prevents an outflow of an analyte sample from a test strip.

An object of the present invention is to provide a device for immunochromatography, which can achieve a smooth development of the analyte sample.

A first aspect of the present invention is a first device for immunochromatography comprising a test strip comprising a sample application member, a label holding member, and a chromatography membrane carrier, where the sample application member is placed to overlap a part of the label holding member, a first case member placed on a first surface side of the test strip and comprising a first protrusion and a second protrusion, said first protrusion and said second protrusion being placed in a development direction of the test strip and a second case member placed on a second surface side of the test strip, comprising a third protrusion that opposes the first protrusion and second protrusion, and attachable to the first case member so as to form a case for housing the test strip, wherein the test strip is held by the first and third protrusions in a region where the label holding member and the sample application member overlap each other.

A second aspect of the present invention is a first detection kit including the first device for immunochromatography and a liquid for pretreatment of a specimen.

A third aspect of the present invention is a first method for testing an analyte substance including a step of preparing a specimen and a step of testing the analyte substance by using the first device for immunochromatography.

A fourth aspect of the present invention is a second method for testing an analyte substance including a step of preparing a specimen, a step of treating the specimen with a specimen pretreatment liquid, and a step of testing the analyte substance by using the first device for immunochromatography.

A fifth aspect of the present invention is a second device for immunochromatography comprising, a test strip comprising a sample application member, a label holding member, and a chromatography membrane carrier, an absorbent member placed to overlap a part of the chromatography membrane carrier, a first case member placed on a first surface side of the test strip and comprising a first protrusion and a second protrusion, said first protrusion and said second protrusion being placed in a development direction of the test strip and a second case member placed on a second surface side of the test strip, comprising an absorbent member positioning protrusion and attachable to the first case member so as to form a case for housing the test strip.

A sixth aspect of the present invention is a second detection kit including the second device for immunochromatography and a liquid for pretreatment of a specimen.

A seventh aspect of the present invention is a third method for testing an analyte substance including a step of preparing a specimen and a step of testing the analyte substance by using the second device for immunochromatography.

A eighth aspect of the present invention is a third device for immunochromatography comprising a test strip comprising a sample application member, a label holding member, and a chromatography membrane carrier, where the sample application member is placed on a part of the label holding member, an absorbent member placed on a part of the chromatography membrane carrier, a first case member placed on a first surface side of the test strip, comprising a first protrusion, a second protrusion, a third protrusion and a fourth protrusion, said first to fourth protrusions being placed in the development direction of the test strip, and a second case member placed on a second surface side of the test strip comprising a fifth protrusion and an absorbent member positioning protrusion and attachable to the first case member so as to form a case for housing the test strip, said fifth protrusion opposing the first protrusion and the second protrusion, wherein the test strip is held by the first and fifth protrusions in a region where the label holding member and the sample application member overlap each other.

BRIEF DESCRIPTION OF THE DRAWINGS

FIG. 3A shows a state in which the case is closed: FIG. 3B shows a state in which the case is open to the left side;

FIG. 4A is a view illustrating a state in which the test strip is pressed by the protrusions of the test strip case: FIG. 4B is a view illustrating a state in which the test strip is not pressed by protrusions of the test strip case;

FIG. 5A is a view illustrating a state in which the test strip is pressed by the protrusions of the test strip case: FIG. 5B is a view illustrating a state in which the test strip is not pressed by protrusions of the test strip case;

FIG. 7A shows a state in which the case is closed: FIG. 7B shows a state in which the case is open to the left hand side.

DETAILED DESCRIPTION OF THE DRAWINGS AND THE PRESENTLY PREFERRED EMBODIMENTS (Immunochromatography)

Figure 1:
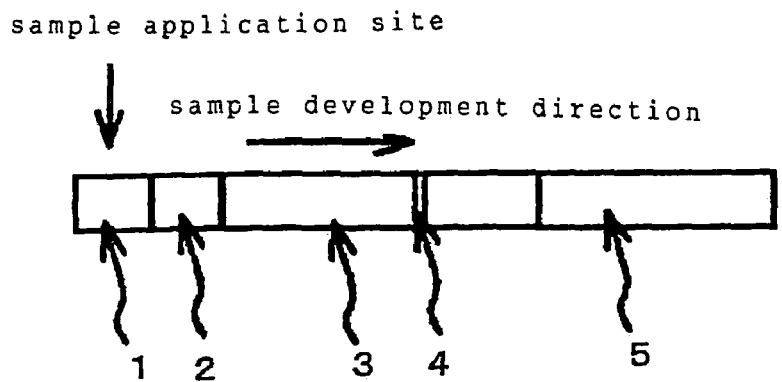
FIG. 1 is a view schematically illustrating a test strip for immunochromatography.

The technique of immunochromatography is already known in the art. The principle thereof will be described by schematically illustrating one example of a test strip in FIG. 1. Here, the test strip represents a main body at which the immunochromatography is actually carried out and which is provided with a sample application member 1, a label holding member 2, a chromatography membrane carrier 3, a detection capturing site 4, and others in accordance with the needs. When the analyte substance is an antigen, the label holding member 2 of FIG. 1 is let to hold a ligand (i.e. an antibody) labeled with colored particles and corresponding to the antigen. An antibody that recognizes the epitope of the antigen, for example, is fixed to the detection site 4. A pretreated specimen is dropped as a sample onto the sample application member 1 of FIG. 1, and the sample is developed towards the absorbent member 5 via the chromatography membrane carrier 3. If the specimen contains an antigen which is the analyte substance, the antigen, the antibody labeled with colored particles, and the antibody fixed to the detection site 4 undergo antigen-antibody reaction and a band of the colored particles appears as a signal at the place of the detection site 4 by reaction of the label. One can schematically grasp the amount of the analyte substance contained in the specimen by the color tone or the like of the band appearing at the detection site 4. Here, it is known in this field of the art that an enzyme, a radioactive substance, a fluorescent substance, or the like can be used besides the aforesaid colored particles as the label. Methods of measuring the signal based on the label is also known in the art.

Further, on the sample development ending side of the chromatography membrane carrier 3 of the test strip of FIG. 1, an absorbent member 5 is placed to overlap the chromatography membrane carrier 3. In order to improve the absorbency, the absorbent member 5 preferably has a larger width than the test strip.

Here, in the Example, the absorbent member is provided separately from the test strip; however, the test strip may be provided with an absorbent member.

The antibodies used in the label holding member 2 and the detection site 4 may be antibodies that recognize different sites of the analyte substance. These antibodies can be obtained by a method generally used. For example, one may employ a method of establishing a hybridoma by cell fusion by Kohler and Milstein (Kohler G, C. Milstein, Continuous cultures of fused cells secreting antibody of predefined specificity, Nature, 256:495-497, 1975). Alternatively, one may simply immunize an animal with an antigen and purify its blood serum. As the label colored particles used in the label holding member 2, known ones used in immunochromatography can be used. For example, colored latex particles can be used.

The chromatography membrane carrier 3 may be a membrane generally used in immunochromatography, and is generally a porous membrane. Specifically, one can make use of a nitrocellulose membrane.

(Device for Immunochromatography)

Figure 2:
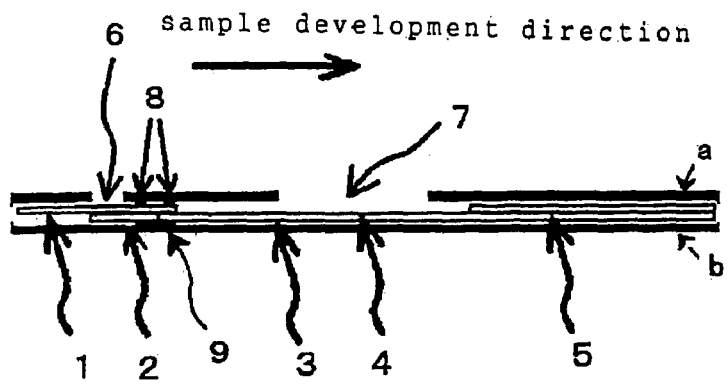
FIG. 2 is a view schematically illustrating a device for immunochromatography.
Figure 3:
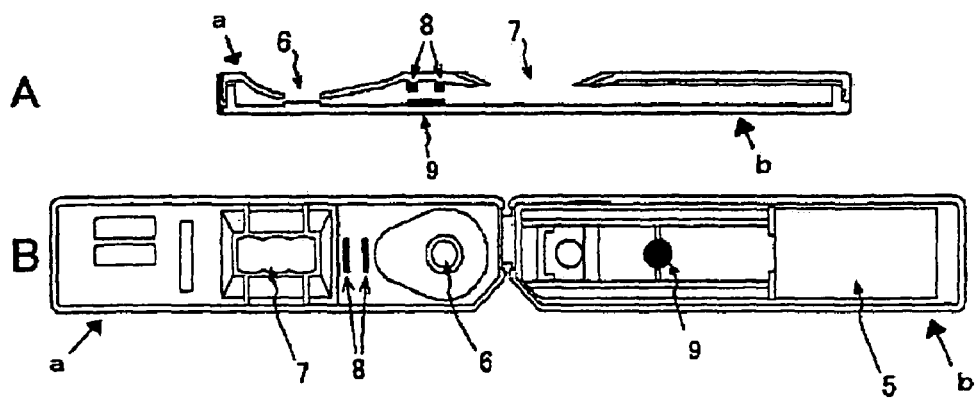
FIGS. 3A and 3B are views illustrating a test strip case.

A device for immunochromatography represents a device having a structure such that a test strip is sandwiched between an upper case member (a) that covers the upper surface of the test strip and a lower case member (b) that covers the lower surface of the test strip (See FIG. 2). A test strip case (which may be hereafter simply referred to as "case") represents a case including the upper case member (a) that covers the upper surface of the test strip and the lower case member (b) that covers the lower surface of the test strip (See FIG. 3). The material of the case is not particularly limited, so that a material already widely used or a material that will be used in the future can be employed. Specifically, one can make use of a material generally referred to as plastics such as polypropylene or ABS.

The test strip used in the device for immunochromatography may have a structure known in the art. It is preferable that the sample application member and the label holding member are placed to overlap each other at least partly. For example, the sample application member 1 may be placed to cover the label holding member 2, and the sample application member 1 may be longer than the label holding member 2 and may also overlap a part of the chromatography membrane carrier 3 (See FIG. 4). Alternatively, the sample application member 1 may be placed to overlap the label holding member 2, and the length of the sample application member 1 may be adjusted to be substantially equal to the length of the label holding member 2 in the sample development direction of the test strip, whereby the sample application member 1 and the label holding member 2 overlap each other (See FIG. 5). Further, the length of the sample application member 1 may be shorter than the length of the label holding member 2 in the sample development direction of the test strip as long as a part of the sample application member 1 overlaps the label holding member 2.

In the device for immunochromatography, the upper case member (a) of the case is provided with at least two protrusions 8 in the sample development direction so as to establish close adhesion between the sample application member 1 and the label holding member 2 of the test strip, and further the lower case member (b) is provided with a protrusion 9 that opposes the aforesaid two protrusions 8 provided in the upper case member (a).

The at least two protrusions 8 provided in the upper case member (a) for pressing the sample application member may be provided to collaborate with the protrusion 9 so as to establish close adhesion at least between the sample application member 1 and the label holding member 2. Alternatively, depending on the case, the at least two protrusions 8 may be provided to establish close adhesion further between one end of the sample application member 1 and one end of the chromatography membrane carrier 3. Since these protrusions establish the close adhesion between a part of the sample application member 1 and the label holding member 2, the sample dropped onto the sample application member 1 is efficiently supplied to the label holding member 2. Further, the protrusion 9 prevents the test strip from closely adhering to the lower case member (b), thereby preventing the outflow of the sample along the interface between the test strip and the lower case member (b). Thus, the test strip is held by the protrusion 8 and the protrusion 9 in a region where the label holding member 2 and the sample application member 1 overlap each other. The size of the protrusions provided in the upper case member (a) is not particularly limited; however, the protrusions can fully exhibit their function, for example, with a height of 0.4 to 3.0 mm, preferably 0.8 to 2.0 mm. The lateral width thereof may be a length of about the width of the test strip. The width thereof in the development direction is not particularly limited and may be of a degree such that the aforesaid function can be exhibited. Specifically, a width of 0.5 to 4.0 mm, preferably 0.5 to 2.0 mm, is sufficient.

The protrusion 9 provided in the lower case member (b) to oppose the aforesaid sample application member pressing protrusions 8 may be placed at a position where all or part of the protrusion 9 overlaps the sample application member pressing protrusions 8 when the upper case member (a) is superposed upon the lower case member (b) for carrying out immunochromatography. The shape thereof is not particularly limited; however, the protrusion 9 may have a cylindrical shape with a height of 0.3 to 2.5 mm and a diameter of 2 to 20 mm or a quadrangular prismatic shape with a side of 2 to 20 mm.

A different embodiment will be described with reference to FIGS. 6 and 7.

The lower case member (b) is provided with an absorbent member mounting part for placing an absorbent member at an appropriate position relative to the test strip and a protrusion 11 for positioning the absorbent member. Further, in order to allow the absorbent member mounted on the absorbent member mounting part to closely adhere to the test strip, the upper case member (a) is provided with at least two absorbent member pressing protrusions 10 in the sample development direction. This construction prevents shift of the absorbent member in the case, improves the close adhesion between the absorbent member and the chromatography membrane carrier, and stabilizes the sample absorption effect. Furthermore, in order to improve the absorbency, it is preferable to use an absorbent member having a larger width than the test strip. Further, both of the two absorbent member pressing protrusions 10 are placed in the upper case member (a) so as to press the absorbent member in a region where the chromatography membrane carrier and the absorbent member overlap each other. This construction further improves the close adhesion between the absorbent member and the chromatography membrane carrier. In addition, one of the two absorbent member pressing protrusions 10 located on an upstream side of the sample development direction is placed at a position that is close to the absorbent member positioning protrusion 11 in the sample development direction. This construction allows that, even if the absorbent member is set to override partly on the absorbent member positioning protrusion 11 at the time of assembling the device for immunochromatography, the absorbent member is sandwiched between the absorbent member positioning protrusion 11 and the one absorbent member pressing protrusion 10 located on the upstream side of the sample development direction, thereby inhibiting engagement of the upper case member and the lower case member. This prevents poor assemblage of the device. Such an absorbent member pressing protrusion 10 of the upper case member protrudes downward from the upper case member. Here, the one absorbent member pressing protrusion 10 located on the upstream side of the sample development direction is disposed on the downstream side of the sample development direction relative to the absorbent member positioning protrusion 11. At this time, it is preferable that the distance in the sample development direction between the one absorbent member pressing protrusion 10 located on the upstream side of the sample development direction and the absorbent member positioning protrusion 11 is less than the thickness of the absorbent member. The size of the protrusions is not particularly limited; however, the protrusions can fully exhibit their function, for example, with a height of 0.4 to 3.0 mm, preferably 0.8 to 2.0 mm. The width thereof may be larger than the width of the test strip. The width thereof in the development direction is not particularly limited and may be of a degree such that the aforesaid function can be exhibited. Specifically, a width of 0.5 to 4.0 mm, preferably 1.0 to 3.0 mm, is sufficient.

(Analyte, Specimen, Sample)

The analyte may be one that can be detected by immunochromatography technique, and is not particularly limited. Specifically, examples of the analyte include cells, protein, glycoprotein, enzymes, polysaccharides, bacteria, and virus.

The specimen is not particularly limited and may be one that possibly contains any one of the analytes that can be measured by immunochromatography technique. Specifically, examples of the specimen include saliva, blood, plasma, serum, urine, sweat, tears, snivel, phlegm, and/or throat swab liquid. The collected specimen may be pretreated so as to have a suitable shape, molecular condition, and the like for testing. In this specification, the pretreated specimen is referred to as "sample".

(Kit)

Further, the present invention extends over to a detection kit for immunochromatography including the aforesaid device for immunochromatography and reagents needed for the immunochromatography. Specifically, a detection kit may be made of a pretreatment liquid and a device for immunochromatography, and may further include a swab or the like for collecting a specimen.

EXAMPLES

For understanding of the present invention, Examples based on FIGS. 3 to 7 will be hereafter shown and described; however, the present invention is not limited to these Examples.

Example 1

A case for a test strip in a device for immunochromatography will be described (hereafter simply referred to as "case"). FIG. 3A shows a state in which the case is closed, and FIG. 3B shows a state in which the case is open to the left side.

Polypropylene was used as a material for the test strip case. Two sample application member pressing protrusions 8 having a height of 1 mm and a width of 1×5 mm were disposed in the upper case member (a) to protrude downwards therefrom. A cylindrical protrusion 9 having a height of 0.4 mm and a diameter of 4.2 mm was disposed in the lower case member (b) to protrude upwards therefrom.

Example 2

The device for immunochromatography schematically refers to the one shown in FIG. 2 where a test strip shown in FIG. 1 is placed on the lower case member of FIG. 3B, and the upper case is closed as shown in FIG. 3A.

Figure 4:
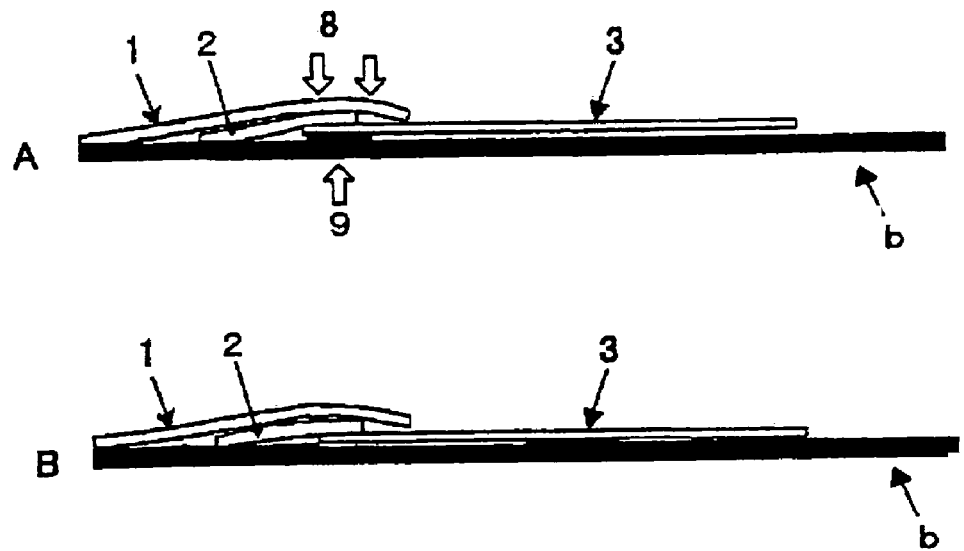
FIGS. 4A and 4B illustrate test strips mounted on a device for immunochromatography, showing a mode in which a sample application member 1 covers a label holding member 2.

Regarding the test strip mounted on the case for immunochromatography, this Example shows a mode in which the sample application member 1 covers the label holding member 2 (FIG. 4). The test strip used in this Example is such that the sample application member 1 is made of a glass fiber filter; the label holding member 2 is made of a polyvinyl-treated glass fiber filter that holds a commercially available anti-influenza antibody labeled with blue latex particles; the chromatography carrier membrane 3 is made of a nitrocellulose membrane; and the absorbent member 5 is made of a mixed paper of glass fiber and cellulose. Further, an anti-influenza antibody is fixed to the detection site 4.

Two sample application member pressing protrusions 8 protruding downwards from the upper case were disposed, one at a position where the sample application member 1 and the label holding member 2 overlap each other in close adhesion, and the other at a position where the sample application member 1 and the chromatography membrane carrier 3 overlap each other in close adhesion. Further, a protrusion 9 protruding upwards from the lower case was disposed at a position that opposes the two sample application member pressing protrusions 8 protruding downwards from the upper case (FIG. 4A). Since these sample application member pressing protrusions 8 and protrusion 9 are provided, the sample application member 1, the label holding member 2, and the chromatography membrane carrier 3 partially adhere to one other. On the other hand, when these sample application member pressing protrusions 8 and protrusion 9 are not provided, the sample application member 1, the label holding member 2, and the chromatography membrane carrier 3 do not sufficiently adhere to one other (FIG. 4B).

Immunochromatography is carried out when a sample is applied through a sample application inlet 6 to the sample application member 1 and the applied sample is developed through the label holding member 2 onto the chromatography membrane carrier 3.

Example 3

Figure 5:
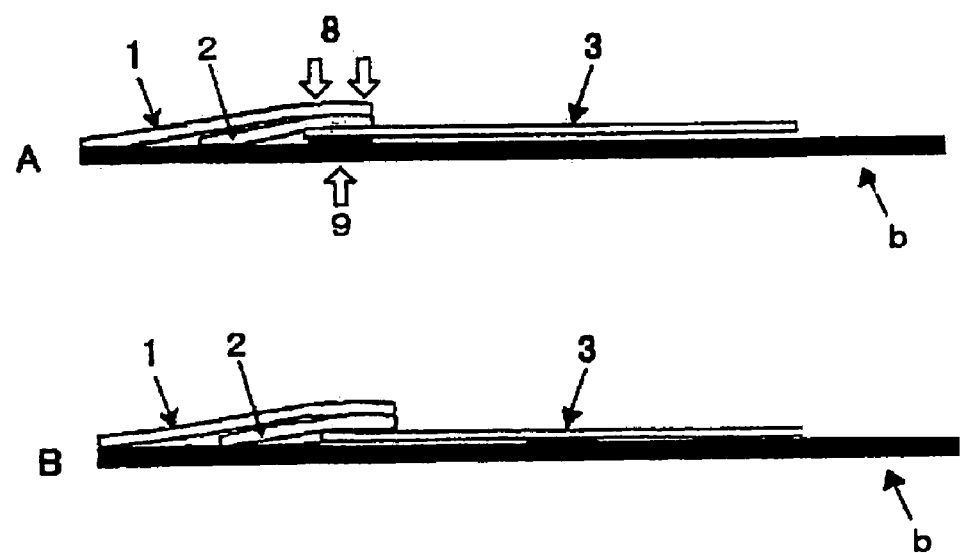
FIGS. 5A and 5B illustrate test strips mounted on a device for immunochromatography, showing a mode in which a sample application member 1 overlaps a label holding member 2.

Regarding the test strip mounted on the case for immunochromatography, this Example shows a mode in which the sample application member 1 and the label holding member 2 overlap each other (FIG. 5). The test strip used in this Example was obtained by processing the test strip used in Example 2.

Two sample application member pressing protrusions 8 protruding downwards from the upper case are disposed at positions where the sample application member 1 and the label holding member 2 overlap each other in close adhesion. Further, a protrusion 9 protruding upwards from the lower case is disposed at a position that opposes the two sample application member pressing protrusions 8 protruding downwards from the upper case (FIG. 5A). Since these sample application member pressing protrusions 8 and protrusion 9 are provided, the sample application member 1, the label holding member 2, and the chromatography membrane carrier 3 partially adhere to one other. On the other hand, when these sample application member pressing protrusions 8 and protrusion 9 are not provided, the sample application member 1, the label holding member 2, and the chromatography membrane carrier 3 do not sufficiently adhere to one other (FIG. 5B).

Experiment Example 1

The effect of chromatography using the device for immunochromatography was examined by using background defect as an index. Here, the background defect refers to a state in which the chromatography membrane carrier remains colored in blue at the time of judgment, making it impossible to distinguish a blue colored line from the background.

A snivel specimen confirmed to be influenza-positive by cultivation was pretreated by an ordinary method to prepare a sample. Pattern A represents a case in which the device for immunochromatography (FIG. 4A) provided with protrusions shown in Example 2 was used, whereas pattern B (comparison) represents a case in which the device for immunochromatography (FIG. 4B) not provided with protrusions was used.

The above-described sample was dropped onto each device for immunochromatography to carry out immunochromatography for 20 minutes. The immunochromatography was carried out for 20 times for each of pattern A and pattern B (comparison). The results are shown in 1. In the device without having protrusions (pattern B) (FIG. 4B), background defect appeared 7 times out of 20 times, whereas in the device having protrusions (pattern A) (FIG. 4A), background defect did not appear at all.

TABLE 1

|  | Background Defect |
|---|---|
| Pattern A | 0/20 |
| Pattern B | 7/20 |

As will be understood from the above description, in the device for immunochromatography, the sample application member pressing protrusions 8 and protrusion 9 provided in the case maintain the close adhesion of the sample application member 1, latex holding member 2, and chromatography membrane carrier 3 and, by raising the test strip up from the lower case member (b), the background defect due to outflow of the sample is effectively prevented.

Example 4

In this Example, a case for a test strip in a device for immunochromatography according to the present invention will be described (hereafter simply referred to as "case"). FIG. 7A shows a state in which the case is closed, and FIG. 7B shows a state in which the case is open to the left side.

Polypropylene was used as a material for the test strip case. Two protrusions 10, one having a height of 1.5 mm and a width of 10.5 mm and the other having a height of 1.5 mm and a width of 6.2 mm, were disposed in the upper case member to protrude downwards therefrom.

Figure 6:
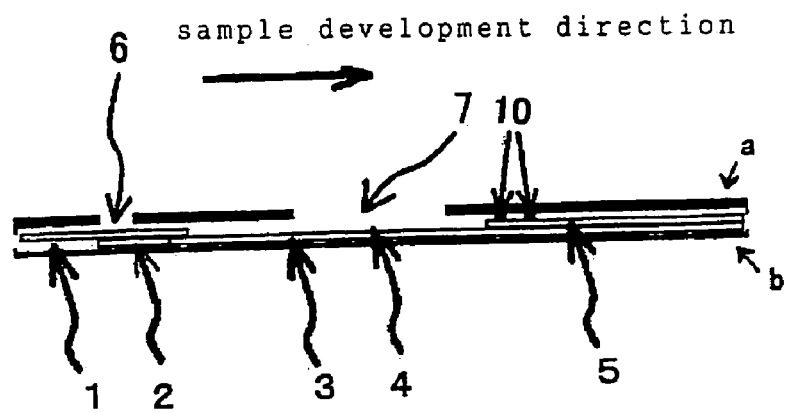
FIG. 6 is a view schematically illustrating a device for immunochromatography having absorbent member pressing protrusions.
Figure 7:
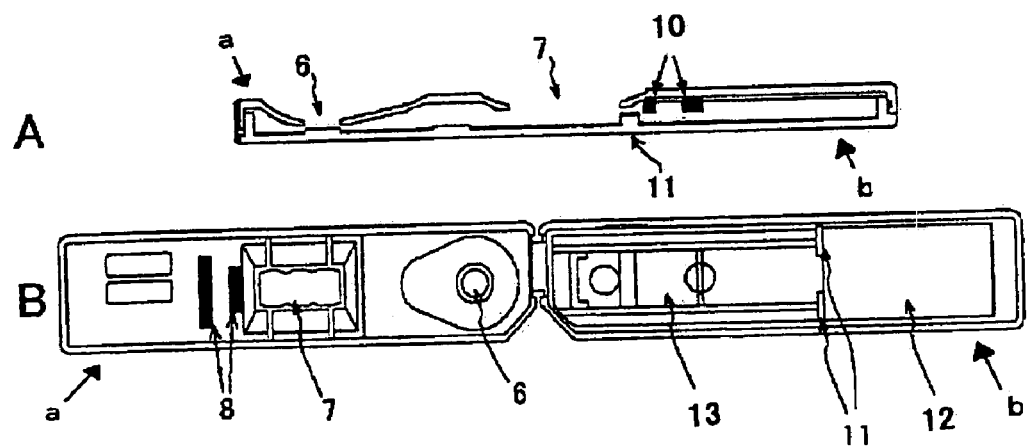
FIGS. 7A and 7B are views illustrating a test strip case having absorbent member pressing protrusions.

The device for immunochromatography in this Example schematically refers to the one shown in FIG. 6 where a test strip shown in FIG. 1 and an absorbent member 5 are placed on the lower case member (b) of FIG. 7B, and the upper case member (a) is closed as shown in FIG. 7A. The lower case member (b) is provided with a test strip placing part 13 for mounting a test strip, an absorbent member mounting part 12 for mounting the absorbent member 5, and an absorbent member positioning protrusion 11. The absorbent member positioning protrusion 11 has a gap, whereby the test strip can be mounted in the gap. The absorbent member mounting part 12 can mount an absorbent member 5 having a larger width than the test strip thereon. The two absorbent member pressing protrusions 10 disposed in the upper case member (a) to protrude downwards are disposed at positions where the absorbent member 5 and the chromatography membrane carrier 3 overlap each other so as to press the absorbent member 5 in close adhesion to the chromatography membrane carrier 3. Further, referring to FIG. 7A, one of the absorbent member pressing protrusions 10 of the upper case member (a) located on the upstream side of the sample development direction is placed at a position that is close to the absorbent member positioning protrusion 11 of the lower case member (b). This allows that, even if the absorbent member is shifted from the absorbent member mounting part 12 and set to override partly on the absorbent member positioning protrusion 11 at the time of assembling the device, the absorbent member is sandwiched between the absorbent member positioning protrusion 11 and the absorbent member pressing protrusion 10, thereby inhibiting engagement of the upper case member (a) and the lower case member (b). This prevents poor assemblage of the device. Regarding the two absorbent member pressing protrusions 10 of the upper case member (a), the one having a height of 1.5 mm and a width of 6.2 mm was disposed on the upstream side of the sample development direction, and the one having a height of 1.5 mm and a width of 10.5 mm was disposed on the downstream side of the sample development direction.

When a sample is applied through a sample application inlet 6 to the sample application member 1, the sample is developed from the sample application member 1 towards the absorbent member 5. At this time, the sample is developed into and absorbed by the absorbent member 5 which is pressed and fixed by the absorbent member pressing protrusions 10.

Experiment Example 2

Sample absorption time was examined using a conventional device for immunochromatography having only one absorbent member pressing protrusion and a device having two absorbent member pressing protrusions.

As materials for a test strip to be mounted in the case, the sample application member 1 is made of a glass fiber filter; the label holding member 2 is made of a polyvinyl-treated glass fiber filter that holds a commercially available anti-influenza antibody labeled with blue latex particles; the chromatography membrane carrier 3 is made of a nitrocellulose membrane. Further, the absorbent member 5 is made of a mixed filter of glass fiber and cellulose. The detection site 4 is sensitized with a commercially available anti-influenza antibody. A specimen confirmed to be influenza-positive by cultivation was pretreated by an ordinary method to prepare a sample, which was then dropped onto each device for immunochromatography to carry out chromatography.

Figure 8:
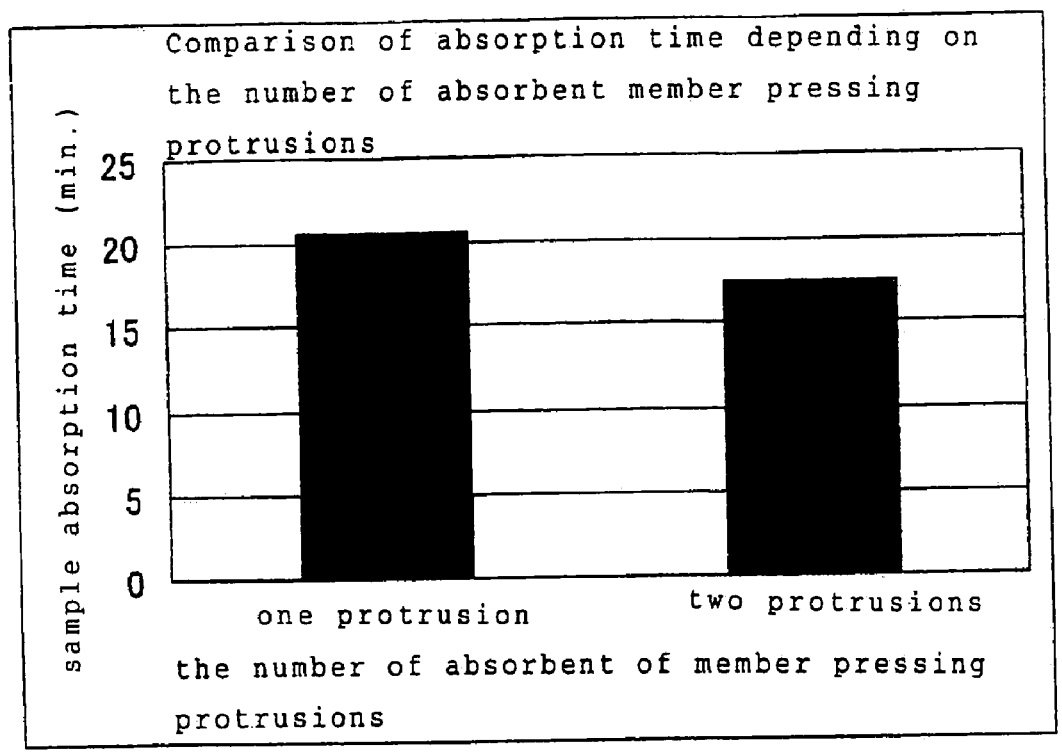
FIG. 8 is a view showing comparison of the sample absorption time in immunochromatography depending on the number of absorbent member pressing protrusions provided in the device.

The speed of sample absorption time was examined by immunochromatography using a test strip case having one or two absorbent member pressing protrusions on the absorbent member 5. As a result of this, as shown in FIG. 8, in the case where one absorbent member pressing protrusion was provided, an average absorption time of 20 minutes and 54 seconds was recognized, whereas in the case where two absorbent member pressing protrusions were provided, an average absorption time of 17 minutes and 41 seconds was recognized. This has confirmed that, by disposing two absorbent member pressing protrusions, the sample is more effectively absorbed.

What is claimed is:

1. A device for immunochromatography comprising:
    a test strip comprising a sample application member, a label holding member configured for holding a labeled ligand against an analyte substance in a sample, and a chromatography membrane carrier comprising a detection site comprising a fixed ligand against the analyte substance;
    a first case member configured for placement on a first surface side of the test strip and comprising a sample application inlet and first and second protrusions configured to project towards the first surface side of the test strip, wherein the first protrusion is arranged a distance upstream from the second protrusion in a development direction of the sample, and wherein the sample application inlet is arranged upstream from the first and second protrusions in the development direction; and
    a second case member configured for placement on a second surface side which is a reverse of the first surface side and comprising a third protrusion configured to project towards the second surface side of the test strip, wherein the third protrusion is opposed to the first and second protrusions and has a width in the development direction spanning the distance between the first and second protrusions so that the third protrusion is configured to hold the second surface side of the test strip and the first and second protrusions are configured to hold the first surface side of the test strip when the second case member is attached to the first case member so as to form a case for housing the test strip;
        wherein the sample application member comprises an overlap region that overlaps a part of the label holding member and a non-overlap region for applying the sample;
        wherein the sample develops from the non-overlap region of the sample application member to the chromatography membrane carrier through the label holding member; and
        wherein the first and third protrusions are configured to hold the test strip in the overlap region of the sample application member when the second case member is attached to the first case member.

2. The device of claim 1, wherein the sample application member is configured to cover the label holding member, and wherein the second and third protrusions are configured to hold the test strip in a second region where the sample application member and the chromatography membrane carrier overlap.

3. The device of claim 1, wherein the second and third protrusions are configured to hold the test strip in the overlap region.

4. A detection kit comprising the device for immunochromatography according to claim 1 and a liquid for pretreatment of a specimen.

5. A method for testing an analyte substance comprising:
treating a specimen with a specimen pretreatment liquid to provide a sample;
applying the sample to the non-overlap region of the sample application member of the device of claim 1, wherein the label holding member comprises a labeled ligand against the analyte substance, wherein the applied sample develops from the non-overlap region to the detection site through the overlap region, and wherein the label holding member and the analyte substance in the developed sample bind to the labeled ligand; and
detecting the analyte substance by capturing analyte substance bound to the labeled ligand with the fixed ligand of the detecting site.

6. The device of claim 1 further comprising an absorbent member placed on a part of the chromatography membrane carrier;
wherein the first case member further comprises fourth and fifth protrusions arranged in the development direction of the sample; and
wherein the second case member further comprises an absorbent member positioning protrusion.

7. The device of claim 6, wherein the sample application member is configured to cover the label holding member, and wherein the second and third protrusions are configured to hold the test strip in a second region where the sample application member and the chromatography membrane carrier overlap.

8. The device of claim 7, wherein the second and third protrusions are configured to hold the test strip in the second region.

9. The device of claim 6, wherein the fourth and fifth protrusions and the second case member are configured to hold the absorbent member and the test strip in a third region where the chromatography membrane carrier and the absorbent member overlap.

10. The device of claim 6, wherein the fourth protrusion is arranged upstream in the development direction of the sample at a position adjacent to the absorbent member positioning protrusion.

11. The device of claim 10, wherein the absorbent member positioning protrusion is configured to inhibit engagement of the first case member and the second case member when the absorbent member is set to override partly on the absorbent member positioning protrusion.

12. The device of claim 6, wherein the absorbent member has a larger width than the test strip.

* * * * *